United States Patent [19]

Rakoczi et al.

[11] Patent Number: 4,845,638
[45] Date of Patent: Jul. 4, 1989

[54] METHOD OF ELIMINATING EXCESS NITRITE IN DIAZOTISATION SOLUTIONS

[75] Inventors: Ferenc Rakoczi, Zurich; Bruno Förtsch, Ramlinsburg, both of Switzerland

[73] Assignee: Ciba-Geigy Corporation, Ardsley, N.Y.

[21] Appl. No.: 883,213

[22] Filed: Jul. 8, 1986

[30] Foreign Application Priority Data

Jul. 15, 1985 [CH] Switzerland .................. 3052/85

[51] Int. Cl.$^4$ .................. G06F 15/46; G05D 7/00
[52] U.S. Cl. .................. 364/500; 364/550; 422/110; 422/119; 534/579
[58] Field of Search .................. 364/500, 550, 200; 422/108, 110, 111, 119, 189, 197; 534/565, 579, 583, 584, 752; 324/453; 556/12

[56] References Cited

U.S. PATENT DOCUMENTS

| | | | |
|---|---|---|---|
| 3,800,288 | 3/1974 | Russell et al. | 364/200 |
| 4,159,264 | 6/1979 | Hamilton et al. | 534/584 |
| 4,233,213 | 11/1980 | Breig et al. | 556/12 |
| 4,246,171 | 1/1981 | Hamilton et al. | 422/108 |
| 4,285,860 | 8/1981 | Hansen et al. | 534/582 |
| 4,294,755 | 10/1981 | Kanter | 534/752 |
| 4,367,173 | 1/1983 | Kanter | 534/752 |
| 4,387,422 | 6/1983 | Steutermann | 422/110 |
| 4,589,072 | 5/1986 | Arimatsu | 364/500 |
| 4,633,413 | 12/1986 | Caveney et al. | 364/500 |
| 4,737,240 | 4/1988 | Davis et al. | 534/583 |

OTHER PUBLICATIONS

Encyclopedia of Chemical Technology, 3rd Ed., vol. 2 (1978).
Encyclopedia of Chemical Technology, 3rd Ed., vol. 8 (1979).
G. Ross Robertson et al–Laboratory Practice of Organic Chemistry, pp. 279–280 (1962).

*Primary Examiner*—Parshotam S. Lall
*Assistant Examiner*—Kevin J. Teska
*Attorney, Agent, or Firm*—Kevin T. Mansfield; Edward McC. Roberts

[57] ABSTRACT

The invention relates to an automatically controlled continuous method of eliminating excess nitrite in diazotization solutions of aromatic amines, which comprises controlling the addition of the agent employed for eliminating the nitrite ions by means of an electrochemically controlled variable.

The process permits a smooth monitoring of the nitrite ion concentration in diazotization solutions. It is advantageous that the determination of the electrochemical controlled variable is almost instantaneous and that the addition of agent for removing nitrite ions can be controlled in simple manner via the fluctuations in the potential.

4 Claims, 1 Drawing Sheet

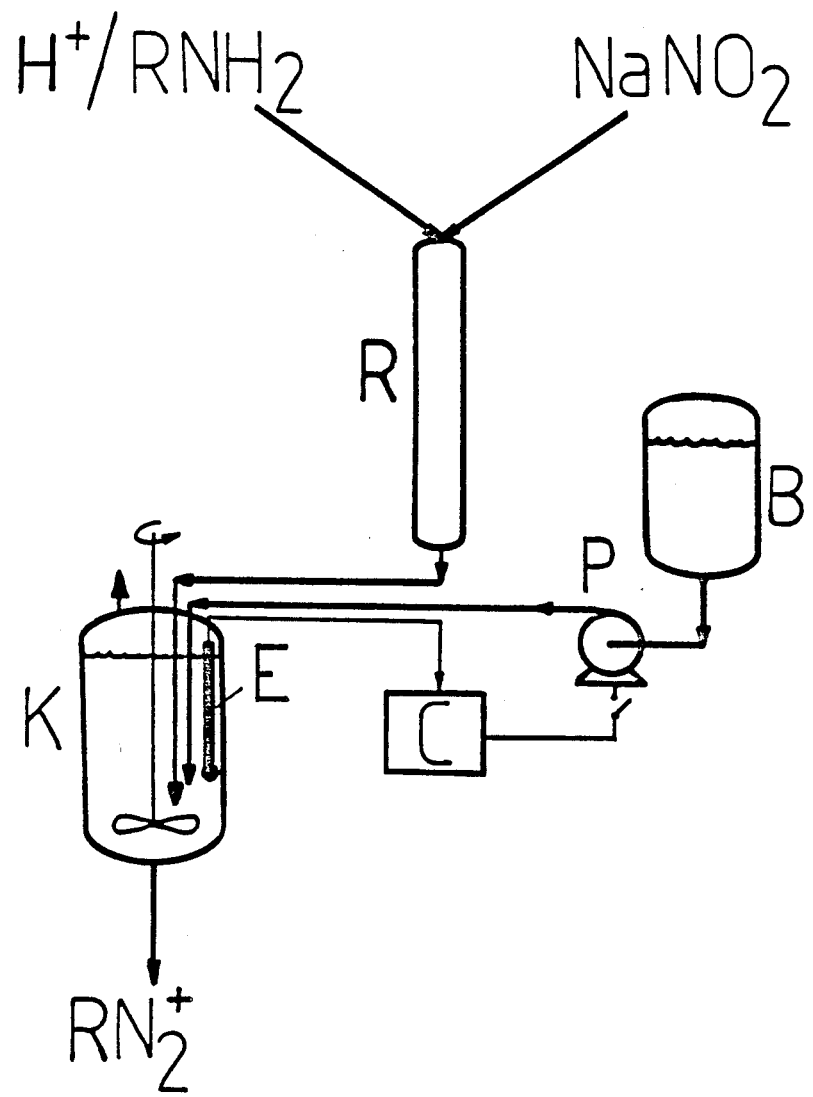

METHOD OF ELIMINATING EXCESS NITRITE IN DIAZOTISATION SOLUTIONS

FIELD OF THE INVENTION

The present invention relates to a continuous method of eliminating excess nitrite in diazotisation solutions, which method is controlled by an electrochemical controlled variable.

BACKGROUND OF THE INVENTION

The usual procedure for the preparation of azo dyes is to diazotise the amine employed as diazo component in a first step and then, in a second step, to react the diazotised amine with the appropriate coupling component. The diazotisation is normally carried out in a mineral acid solution by adding an excess of nitrite, e.g. sodium nitrite. When diazotisation is complete, the excess nitrite must be removed before the azo coupling takes place. This removal is usually effected by adding a small amount of non-diazotised amine or by adding urea or amidosulfonic acid (sulfamic acid). For diazotisation on an industrial scale the rapidly acting sulfamic acid is normally added. However, the drawback of this procedure is that if an excess of sulfamic acid is added, especially where diazonium salts containing strongly negative substituents are obtained, it may result in secondary reactions, e.g. in the reaction of the sulfamic acid with the diazonium salt so that the amine is formed again by rediazotisation (q.v. H. R. Schweizer, Künstliche Organische Farbstoffe und ihre Zwischenprodukte, Springer Verlag 1964, page 182). To avoid this yield-diminishing secondary reaction it is necessary to add the sulfamic acid as accurately as possible in an amount just sufficient to destroy the excess nitrite. Especially in continuous reactions, monitoring the concentration of nitrite in the diazotisation solution by the widely employed spot test on potassium iodide starch paper has not proved at all suitable Hence it is the object of the present invention to provide a method that permits continuous monitoring of the nitrite concentration and a smooth controlled addition of agent for removing nitrite.

SUMMARY OF THE INVENTION

It has now been found that it is possible to determine the concentration of nitrite in diazotisation solutions in simple manner by means of an electrochemical method of analysis, wherein the current-voltage characteristic of suitable electrodes can be utilised directly as controlled variable for regulating the addition of agent for removing nitrate.

Accordingly, the present invention relates to an automatically controlled continuous method of eliminating excess nitrite in diazotisation solutions of aromatic amines, which comprises controlling the addition of the agent employed for eliminating the nitrite ions by means of an electrochemically controlled variable.

DESCRIPTION OF THE INVENTION

Suitable electrochemical methods of analysis are primarily potentiometric, voltrametric or polarographic methods. Among these methods, it is preferred to use the potentiometric method. This method comprises monitoring the change in the redox potential of the diazotisation solution as a function of the nitrite concentration using electrodes of known construction, and subsequently regulating the addition of agent for removing nitrite.

The electrochemical methods of analysis referred to above are known per se and are described e.g. in Kirk-Othmer, Encyclopedia of Chemical Technology, Vol. 2 (1978), page 616 ff. and Vol. 8 (1979), page 662 ff.; Römpps Chemie-Lexikon, Vol. 2 (1981), page 1081 ff. and the literature cited therein. Examples of suitable indicator electrodes are platinum, silver/silver chloride, platinum/calomel or gold/calomel electrodes. A platinum/glass single rod electrode is particularly suitable for use in the process of this invention.

The method of the invention is normally carried out in a voltage range from about 50 to 700 mV, with control being effected within an interval of about 2–10 mV in the range of maximum sharpness of the voltage curve (end point) for the control system.

If the voltage falls to values below this interval, then the addition of agent for removing nitrite is discontinued. If the voltage rises to values above this range, then addition of agent for removing nitrite is recommended. The great advantage of measuring redox potentials resides in the substantially instantaneous indication allied to simple use of the fluctuations of the potential for automatic control purposes. A process control computer is conveniently employed as control means for regulating the pump which adds the agent for removing nitrite.

The excess nitrite is removed with customary agents, preferably sulfamic acid, which is conveniently added in the form of a 0.5 to 1 molar aqueous solution. Urea or p-nitroaniline may also suitably be used; but nitroaniline is only suitable if the shade of the dye will not thereby be adversely affected.

A further advantage of using sulfamic acid is that, when added intermittently and at a constant rate, it keeps the electrode clean. This kind of addition, in which a small excess of sulfamic acid is briefly present in the diazotisation solution, can be readily made by on/off feed-back control. In this context, a constant rate of addition shall be understood as meaning that a constant amount of sulfamic acid solution is added to the diazotisation solution per unit of time, provided the metering pump is switched on (position: on), i.e. that the voltage has risen to values above the interval. In addition to the potentiometric method preferably employed in this invention, suitable electrochemical methods are—as mentioned at the outset—e.g. the polarographic or voltametric method. This last mentioned method is carried out for example using two platinum electrodes which are polarised by a constant current. If excess nitrite is present, the electrodes are depolarised, which is reflected in a sharp drop in voltage. This drop in voltage is utilised to regulate the pump or valve by means of which the requisite amount of agent for removing nitrite is added to the diazotisation solution. The control system is here to adjusted to a point on the sharp drop in voltage that corresponds more or less to the equivalence point.

DESCRIPTION OF THE DRAWING

The procedure is for example (see drawing) that the diazo component (RNH$_2$·) is diazotised continuously with sodium nitrite in a tube reactor R and the nitrite-containing diazotisation solution is subsequently passed into a stirred vessel K. The addition of sulfamic acid, controlled by the potential, is made simultaneously from the storage vessel B. The stirred vessel K is equipped with an electrode E (platinum/glass single rod electrode). The fluctuations in potential measured by means of this electrode are processed by the process control computer C which, via a corresponding control signal, regulates the pump P which pumps the aqueous solution of sulfamic acid into the stirred vessel. The reaction of nitrous acid with the sulfamic acid then takes places at a temperature in the range from 10° to 50° C., although higher temperatures may also be chosen according to the stability of the diazonium salt. As substantial amounts of nitrogen are evolved, it is advisable to carry out the process in an open vessel, especially as the diazonium salt solutions have a tendency to foam fairly strongly. The residence time of the diazotisation solution in the stirred vessel is about 1 to 30, usually 3 to 10, minutes. Diazonium salt solution ($RN_2+$) which is free from nitrite is drawn off continuously from the stirred vessel and, if necessary, subsequently clarified by filtration and then coupled to a suitable coupling component. The method is susceptible of application to all amines which can be diazotised in acid aqueous media.

A suitable, fully electronic, microprocessor-controlled device for controlling a pump or other device in response to a fluctuating electrical signal is the Capax 5SO (Camille Bauer AG, Wohnen, Switzerland).

DESCRIPTION OF THE PREFERRED EMBODIMENTS

In particular, the method of the present invention can be used for the preparation of azo dyes, preferably for the continuous preparation of azo dyes. The preferred utility is as part of an on-line control of a computer-integrated, automated process for the preparation of azo dyes.

Examples of suitable diazo components are: amiline and derivatives thereof such as 4-nitroaniline, 3-nitroaniline, 2-chloro-4-nitroaniline, 4-chloro-2-nitroaniline, 2,6-dichloro-4-nitroaniline, 4-aminoacetanilide, 2,4-dinitroaniline, 2-cyano-4-nitroaniline, 4-cyanoaniline, 4-chloroaniline, 2,4,5-trichloroaniline, 2,5-dimethoxyaniline, o-anisidine, p-anisidine, o-phenetidine, p-phenetidine, o-toluidine, p-toluidine, 4-nitro-2-aminoanisole, 2-nitro-4-aminoanisole, p-phenoxyaniline, or also 4-methylsulfonylaniline, 4-amino-2, 4-dichlorobenzophenone, 4'-amino-2,4-dinitro-benzophenone, 2-nitroaniline, 2-chloro-4, 6-dinitroaniline, 2, 5-dichloroaniline, 3, 3'-dichlorobenzidine, 5-nitro-2-amino-anisole, 3-nitro-4-aminotoluole, 2, 4-dichloroaniline, 3-nitro-4-aminoanisole, 2-aminoanisole-4-sulfodietylamide, 5-chloro-2-aminotoluene, 4-chloro-2-aminotoluene, 4-nitro-2-aminotoluene, 5-nitor-2-aminotoluene, 4-nitro-2-aminoanisole, 3, 3-dimethoxybenzidine, 3, 3'-dimethyoxy-6, 6'-dichlorobenzidine, 2-amino-4-chlorophenol, 2-aminophenol-4-sulfamide, 2-aminophenol-5-sulfamide, 2-aminophenol-4-sulfomethylamide, 3-amino-4-hydroxyphenylmethylsulfone, 2-amino-5-nitrophenylmethylsulfone, 4-amino-3-nitrophenylmethylsulfone, 2-(N-methyl-N-cyclohexylsulfamoyl)aniline, 2-amino-4, 2', 4'-trichlorodiphenyl ether and 4-aminoazobenzene; α- or β-napthylamine, and derivatives thereof, such as 2-naphthylamine-6, 8-disulfonic acid, 1-naphthylamine-3, 6, 8-trisulfonic acid, 4-naphthylamino-5-hydroxy-1, 7-disulfonic acid or 2-naphthylamino-7-hydroxy-6-sulfonic acid; Examples of further heterocylic amines are: 3-amino-1,2, 4-triazole, 2-aminothiazole, benzthiazoles such as 2-aminobezthiazole, 2-amino-4-chlorobenzthiazole, 2-amino-4-cyanobenzthiazole, 2-amino-4, 6-dinitrobenzthiazole, 2-amino-4-methoxy-6-nitrobenzthiazole, 2-amino-6-methoxyl-1, 3-benzonthiazole or aminobenztriazoles, which may also be appropriately substituted.

The invention is illustrated by the following Example, in which percentages are by weight.

EXAMPLE:

A mixture of 4158.25 g of 4-aminoactanilide (89.0%) and 2588.25 g of aniline (100%) is diazotised continuously in a tube reactor in a hydrochloric acid solution. A 0.5 to 10% excess of nitrite is employed, based on the theoretically required amount. The diazotisation solution containing excess nitrite is introduced into a straight-through reactor, in which the redox potential is measured continuously by means of a platinum/argental single rod electrode. As a function of the potential, an aqueous solution of sulfamic acid is introduced into the straight-through reactor. This addition is made by means of a pump, regulated by a process control computer which switches the pump on and off as required. The addition of sulfamic acid is made such that the potential of the diazo solution is kept within a 10 −30 mV interval in the range of the end point, e.g. from 590 mV to 610 mV. The reaction between the nitrous acid and the sulfamic acid proceeds at room temperature (20°–25° C.) and the adiabatic rise in temperature is about 1° C. The residence time in the straight-through vessel is not less than 3 minutes. It is expedient to ensure that nitrogen evolved in the course of there reaction can escape from the vessel. This method ensures that the diazo solution leaves the straight-through reactor free from nitrite and can then be further processed in known manner to azo dyes.

Even after prolonged operation, no toxic deposits can be observed on the electrode. Comparably good results are obtained by using a platinum/glass electrode instead of the platinum/argental electrode.

Excess nitrite is also removed by the same method from diazotisation solutions of the following amines: 2-chloro-4-nitroaniline, 4-chloro-2-nitroaniline, 4-aminoazobenzene and 3-amino-1, 2, 4-triazole.

By repeating the procedure of this Example, but using the voltametric or polarographic method instead of the potentiometric method, and/or by using urea and/or 4-nitroaniline instead of sulfamic acid, it is also possible to monitor the nitrite ion concentration of diazotisation solutions and to control the amount of agent for removing nitrite.

What is claimed is:

1. An automatically controlled continuous method of eliminating excess nitrite ions in diazotization solutions of aromatic amines, which method comprises controlling the addition of sulfamic acid employed for eliminating said excess nitrite ions after diazotization is essentially complete so as to maintain within a predetermined range a value determined by a potentiometric, voltametric or polarographic method which varies in proportion to said nitrite ion excess and wherein the addition of said sulfamic acid is made intermittently at a constant rate of addition.

2. A method according to claim 1, wherein the control is effected by a potentiometric method and the redox potential of the diazotization is employed as said value.

3. A process for the continuous preparation of azo dyes which comprises the preparation of diazotization solutions of aromatic amines followed by removal of excess nitrite ions after diazotization is essentially complete, wherein the improvement comprises automatically and continuously controlling the addition of sulfamic acid employed for eliminating said excess nitrite ions after diazotization is essentially complete so as to maintain within a predetermined range a value determined by a potentiometric, voltametric or polarographic method which varies in proportion to said nitrite ion excess and wherein the addition of said sulfamic acid is made intermittently at a constant rate of addition.

4. A method of on-line controlling a process for the continuous preparation of azo dyes which comprises the preparation of diazotization solutions of aromatic amines followed by removal of excess nitrite ions after diazotization is essentially complete, wherein the improvement comprises automatically and continuously controlling, by means of a microprocessor-controlled pump or valve, the addition of sulfamic acid complete so as to maintain within a predetermined range a value determined by a potentiometric, voltametric or polarographic method which varies in proportion to said nitrite ion excess wherein the addition of said sulfamic acid is made intermittently at a constant rate of addition.

* * * * *